US00PP34748P2

(12) United States Plant Patent
de Groot

(10) Patent No.: US PP34,748 P2
(45) Date of Patent: Nov. 22, 2022

(54) ***ROSA* 'RUIRJ0110A'**

(50) Latin Name: *Rosa hybrida*
Varietal Denomination: RUIRJ0110A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 17/841,402

(22) Filed: Jun. 15, 2022

(51) Int. Cl.
*A01H 6/74* (2018.01)
*A01H 5/02* (2018.01)

(52) U.S. Cl.
USPC ..... Plt./108

(58) Field of Classification Search
USPC ..... Plt./108, 101
See application file for complete search history.

*Primary Examiner* — Annette H Para
(74) *Attorney, Agent, or Firm* — Cassandra Bright

(57) ABSTRACT

A new and distinct groundcover *Rosa* plant named 'RUIRJ0110A' is disclosed, characterized by abundant magenta, single flowers. Plants are bushy, compact and low growing, suitable for groundcover use. Plants exhibit both good reflowering and abundant production of hips. The new variety is a *Rosa*, normally produced as an outdoor garden or container plant.

1 Drawing Sheet

Latin name of the genus and species: *Rosa hybrida.*
Variety denomination: 'RUIRJ0110A'.

BACKGROUND OF THE INVENTION

The new *Rosa* cultivar is a product of a planned breeding program conducted by the inventor. The cross resulting in this new variety was made in April of 2009 at a nursery in Boskoop, The Netherlands.

The seed parent is the unpatented variety *Rosa* 'Snow Pavement'. The pollen parent is the unpatented variety *Rosa* 'Andre Brichet'. The new variety was selected in November 2011 by the inventor at the same nursery in Boskoop, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Amstelveen, The Netherlands, in March 2012, and has shown that the unique features of this cultivar are stable and reproduced true to type in successive generations.

SUMMARY OF THE INVENTION

The cultivar 'RUIRJ0110A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRJ0110A' These characteristics in combination distinguish 'RUIRJ0110A' as a new and distinct *Rosa* cultivar:

1. Groundcover shrub rose.
2. Abundant magenta single flowers.
3. Abundant hips produced.
4. Good reflowering.
5. Bushy growth habit.

PARENTAL COMPARISON

Plants of the new cultivar 'RUIRJ0110A' are similar to plants of the seed parent in most horticultural characteristics, however, plants of the new cultivar 'RUIRJ0110A' differ in the following:

1. Flowers of the new variety are magenta; flowers of the seed parent are mostly white.
2. Plants of the new variety are more compact than plants of the seed parent.
3. Flowers of the new variety produce less petals than flowers of the seed parent.

Plants of the new cultivar 'RUIRJ0110A' are similar to plants of the pollen parent in most horticultural characteristics, however, plants of the new cultivar 'RUIRJ0110A' differ in the following;

1. Flowers of the new variety are magenta; flowers of the seed parent are white with light pink.
2. The new variety produces more branches than plants of the pollen parent.
3. Plants of the new variety are more compact than plants of the pollen parent.
4. Flowers of the new variety produce less petals than flowers of the pollen parent.

COMMERCIAL COMPARISON

Plants of the new cultivar 'RUIRJ0110A' can be compared to the commercial variety *Rosa* 'BROKRAHAN', unpatented. These varieties are similar in most horticultural characteristics, however 'RUIRJ0110A' differs in the following:

1. This new cultivar reflowers better than this comparator.
2. This new cultivar produces more branches per plant than this comparator.

3. Plants of the new variety are more compact than plants of this comparator.

Plants of the new cultivar 'RUIRJ0110A' can be compared to the commercial variety *Rosa* 'BOKRATRACK', unpatented. These varieties are similar in most horticultural characteristics, however 'RUIRJ0110A' differs in the following:

1. This new cultivar reflowers better than this comparator.
2. This new cultivar produces more hips per plant than this comparator.

BRIEF DESCRIPTION OF THE PHOTOGRAPH

The accompanying photograph illustrates a close up view of the flower. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRJ0110A' plants grown outdoors in Camarillo, Calif. The growing temperature ranged from approximately 15° C. to 28° C. during the day and from approximately 8° C. to 15° C. during the night. Measurements were taken in April and May. General light conditions were very bright, normal sunlight. Measurements and numerical values represent averages of typical plant types.

Botanical classification: *Rosa* 'RUIRJ0110A'.

Market classification: Groundcover shrub rose.

PROPAGATION

Time to initiate roots: 10 days at approximately 25° C.

Time to produce a rooted cutting: 21 days at approximately 25° C.

PLANT

Growth habit: Dense, low growing, groundcover type.

Age of plant described: 1 year.

In a container size: 2 gallon.

Height: 55 cm.

Plant spread: 50 cm.

Branching characteristics:

Length of primary lateral branches: Approximately 15 cm to 22 cm.

Diameter of lateral branches: Approximately 7 mm to 9 mm.

Quantity of lateral branches: 10 to 14 within 6 weeks of emerging from dormancy.

Branching arrangement: Dense, compound.

Branches-young wood:

*Diameter*.—Approximately 5 mm.

*Texture*.—Lightly pubescent.

*Approximately density/quantity of thorns*.—No thorns on youngest growth.

*Color*.—Near RHS Green 138C.

Branches-old wood:

*Diameter*.—Approximately 5 mm to 6 mm.

*Color*.—Near RHS Green 138B. Oldest basal branches near Yellow-Green 147A.

*Texture*.—Densely covered in very small thorns. About 10 to 15 thorns per linear cm.

*Internode*.—4 to 8 cm.

Thorns:

*Shape*.—Deltate.

*Color*.—Near RHS Yellow-Green 1N144B.

*Length*.—2 mm to 3 mm.

*Diameter*.—2 mm at base, 1 mm along 80% of length.

FOLIAGE

Leaf:

*Arrangement*.—Imparipinnate.

*Quantity*.—Approximately 8 to 15 per main branch.

*Average length*.—Approximately 12 cm to 14 cm.

*Average width*.—Approximately 8.5 cm to 9.5 cm.

Leaflet:

*Quantity*.—Most commonly 9 per leaf. Very rarely 7 on lowest occurring foliage.

*Average length*.—Approximately 5.5 cm.

*Average width*.—Approximately 2.5 cm.

*Shape of blade*.—Elliptic.

*Apex*.—Acute.

*Base*.—Broad tapered.

*Margin*.—Very finely serrate.

*Texture of top surface*.—Smooth.

*Texture of bottom surface*.—Smooth.

*Pubescence*.—None observed.

*Leaf internode length*.—2 cm to 4 cm.

*Color*.—Young foliage upper side: Near RHS Yellow-Green 144A. Young foliage under side: Near RHS Green 138A. Mature foliage upper side: Near RHS Green 137A. Mature foliage under side: Near RHS Green 137B.

*Venation*.—Type: Pinnate. Venation color upper side: Near Green 137B. Venation color under side: Near Yellow-Green 145C.

Stipule:

*Length*.—1.5 cm.

*Width*.—4 mm.

*Color*.—Near RHS Green 143A.

*Texture*.—Smooth.

Petiole:

*Length*.—2.0 cm.

*Width*.—2 mm to 3 mm.

*Color*.—Near RHS Yellow-Green 145B.

*Texture*.—Glabrous.

Rachis:

*Length*.—7 cm.

*Width*.—2 mm.

*Color*.—Near RHS Yellow-Green 145B.

*Texture*.—Glabrous.

FLOWER

Natural flowering season: April through October in Southern California.

Begins flowering after how many years/months: 2 months.

Inflorescence type: Multiflora.

Rate of flower opening: Approximately 3 days from bud to fully opened flower.

Flower longevity on plant: 5 to 7 days, after fully opened.

Quantity of flowers: 1 to 3 flowers per flowering axil.

Inflorescence size:

*Diameter*.—Approximately 9 cm.

*Height*.—Approximately 6 cm.

Flower size:
*Diameter*.—Approximately 9 cm.
*Height*.—Approximately 6 cm.
Peduncle:
*Length*.—3 cm.
*Diameter*.—3 mm.
*Color*.—Near RHS Yellow-Green 145B.
*Texture*.—Slightly pubescent.
Petals:
*Petal arrangement*.—Radial, moderately overlapping.
*Length*.—4.0 cm.
*Width*.—4.0 cm.
*Shape*.—Obcordate.
*Margin*.—Entire, slightly undulate.
*Apex*.—Retuse.
*Base*.—Cuneate.
*Petal quantity*.—5 to 6.
*Texture*.—Glabrous all surfaces.
*Color*.—When opening: Upper surface: Near RHS Red-Purple 71A. Base 71B and White N155B. Lower surface: Near RHS Red-Purple 71B. Base White N155B. Fully opened: Upper surface: Near RHS Red-Purple 71A. Base 71B and White N155B. Lower surface: Near RHS Red-Purple 71A. Base 71B and White N155B.
Bud:
*Shape*.—Ovate.
*Length*.—Approximately 3.0 cm.
*Diameter*.—Approximately 1.1 cm.
*Color*.—Near RHS Greyed-Purple 187C.
Sepals:
*Quantity*.—5.
*Length*.—2.5 cm.
*Width*.—5 mm at base.
*Shape*.—Very narrow deltoid.
*Color*.—Interior Surface: Near Green 138C. Exterior Surface: Near Green 138B.
*Texture*.—Softly pubescent.
Receptacle:
*Length*.—7 mm.
*Width*.—9 mm.
*Shape*.—Spherical
*Color*.—Near Green 138B.
Fragrance: Very strong, sweet rose scent.

REPRODUCTIVE ORGANS

Stamens:
*Quantity*.—Average 110 to 130.
*Filament length*.—Average 7 mm.
*Filament color*.—White 155C.
Anthers:
*Length*.—1.5 mm.
*Shape*.—Oblong.
*Color*.—RHS Greyed-Orange 167C.
*Pollen*.—Scant, colored near Greyed-Orange 167C.
Pistil:
*Number*.—Indistinguishable, all individual parts fused into a single conglomerate structure.
*Height*.—4 mm.
*Diameter*.—5 mm.
*Color*.—Near RHS Yellow-Green 150D.

OTHER CHARACTERISTICS

Seeds and fruits: Rose hips produced abundantly.
*Shape*.—Slightly flattened sphere.
*Diameter*.—1.8 cm.
*Height*.—1.5 cm.
*Color*.—Near Yellow-Green a144A.
*Appearance*.—Shiny.

What is claimed is:

1. A new and distinct hybrid cultivar of *Rosa* plant named 'RUIRJ0110A' as herein illustrated and described.

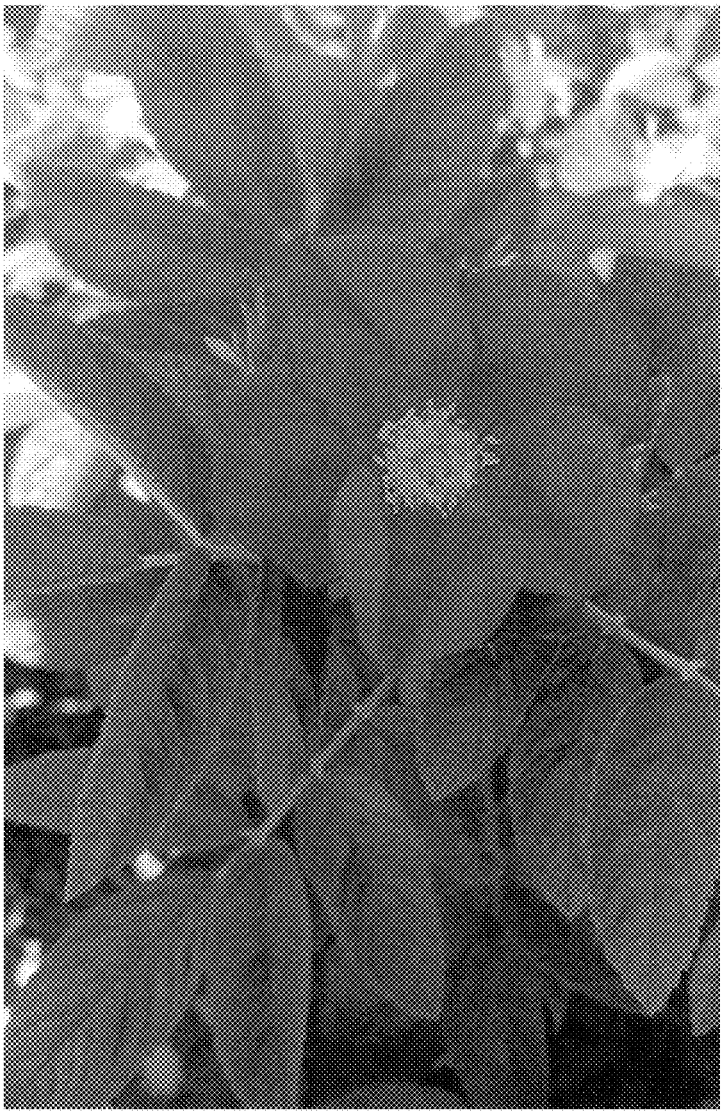

* * * * *